(12) United States Patent
Ying et al.

(10) Patent No.: US 8,343,565 B2
(45) Date of Patent: *Jan. 1, 2013

(54) METHOD FOR PRODUCING GRAPE EXTRACT WITH HIGH ORAC VALUE AND GRAPE EXTRACT SO PRODUCED

(75) Inventors: Weichao Ying, Shaoxing County (CN); Xiaoyan Xiong, Santa Clara, CA (US); Jiaomei Chen, Shaoxing (CN); Jianying Yang, Yuachong District (CN)

(73) Assignee: Ethical Naturals, Inc., San Anselmo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/134,692

(22) Filed: Jun. 14, 2011

(65) Prior Publication Data

US 2011/0250344 A1 Oct. 13, 2011

Related U.S. Application Data

(63) Continuation of application No. 12/287,995, filed on Oct. 14, 2008, now Pat. No. 7,959,963.

(30) Foreign Application Priority Data

Jul. 21, 2008 (CN) .......................... 2008 1 0135896

(51) Int. Cl.
*A23L 1/29* (2006.01)

(52) U.S. Cl. .......................... 426/648; 426/430; 426/544

(58) Field of Classification Search .................. 426/554, 426/430, 544

See application file for complete search history.

(56) References Cited

U.S. PATENT DOCUMENTS

| | | | | |
|---|---|---|---|---|
| 6,099,854 | A * | 8/2000 | Howard et al. | 424/440 |
| 7,767,235 | B2 * | 8/2010 | Shrikhande et al. | 424/766 |
| 7,959,963 | B2 * | 6/2011 | Ying et al. | 426/554 |
| 2005/0048143 | A1 * | 3/2005 | McAnalley et al. | 424/729 |
| 2008/0044539 | A1 * | 2/2008 | Perlman et al. | 426/542 |
| 2009/0110789 | A1 * | 4/2009 | Mower et al. | 426/330.5 |

* cited by examiner

*Primary Examiner* — Anthony Weier

(57) ABSTRACT

Grape material is processed to yield a grape extract high in concentrated polyphenols, with ORAC values exceeding at least about 10,000 μmol TE/g. The grape material is dried, and soaked in ethanol to commence desired concentrate extraction. Following ethanol removal, inactive residue is at least partially separated from the desired concentrate solution, which passes through a macroporous absorption resin that absorbs desired active ingredients. Ethanol resin washing yields an intermediate extraction solution. After ethanol removal, the intermediate extract solution with the mixed active ingredients is refined. During refinement, high concentration of polyphenols and monomeric phenols are separated, and collected. These collected materials yield a desired high ORAC extract solution. Further drying yields the desired material, which is tested and packaged. This material exhibits good water solubility, mild flavor, and can be added to foodstuffs and nutritional supplements as a beneficial antioxidant.

22 Claims, 1 Drawing Sheet

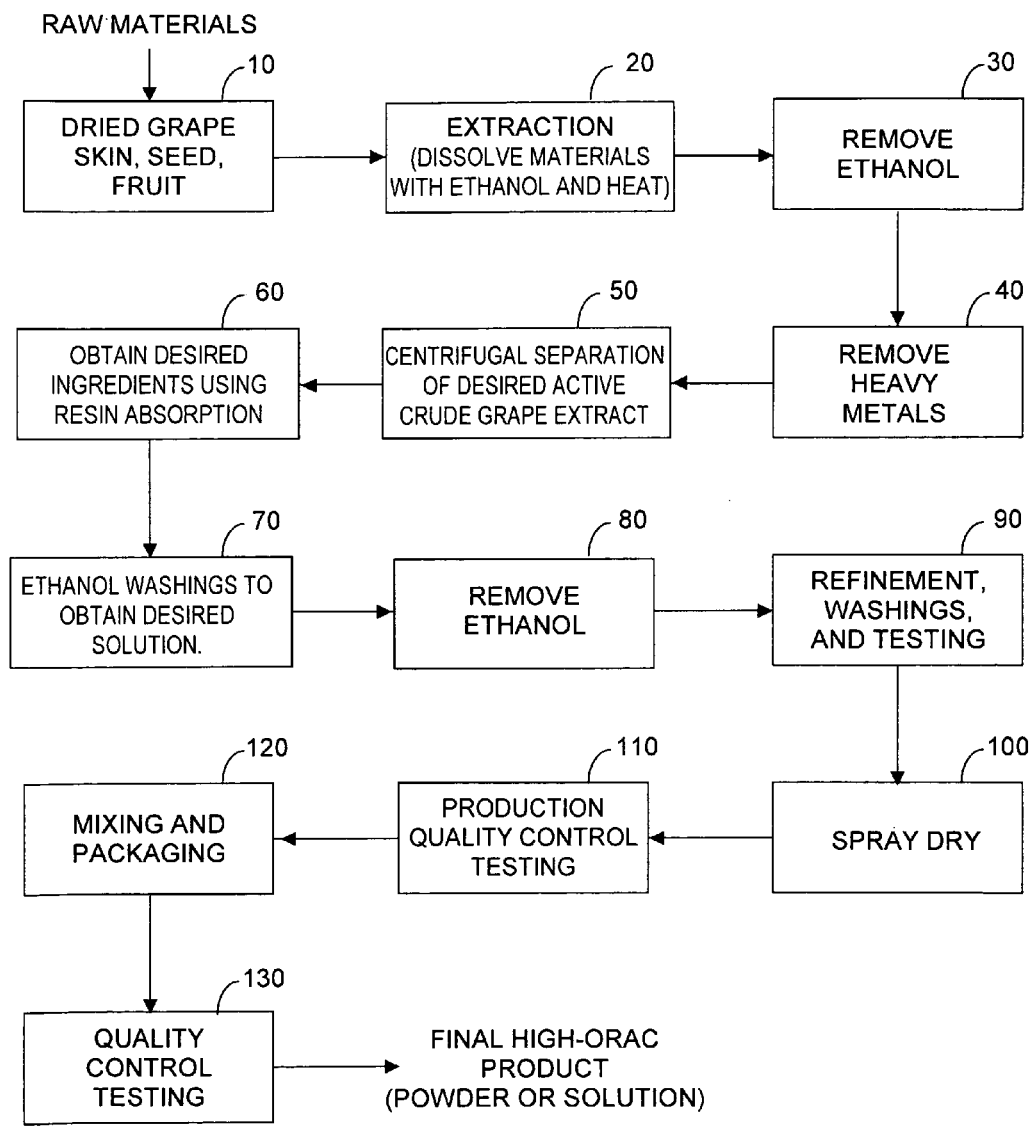

METHOD FOR PRODUCING GRAPE EXTRACT WITH HIGH ORAC VALUE AND GRAPE EXTRACT SO PRODUCED

RELATIONSHIP TO CO-PENDING APPLICATION

This is a continuation application from U.S. application Ser. No. 12/287,995, filed 14 Oct. 2008 entitled "Method for Producing Grape Extract With High ORAC Value, and Grape Extract So Produced", now U.S. Pat. No. 7,959,963. The parent '995 patent application claimed priority to still pending Chinese patent application serial number 200810135896.9, filed 21 Jul. 2008 and bearing the same title (translated) as the within application and the U.S. parent application.

FIELD OF THE INVENTION

The present invention relates generally to production of dietary supplements high in antioxidants, and more specifically to use of grape extracts to produce such supplements with high oxygen radical absorbance capacity (ORAC) value/scores in the range of about 10,000 μmol TE/g and preferably at least about 10,000 to about 30,000 μmol TE/g. (Unless otherwise stated, it is assumed herein that ORAC values or scores are given in units of μmol TE/g.)

BACKGROUND OF THE INVENTION

Humans have long sought to retard the aging process. Today it is widely accepted that antioxidants, e.g., molecules that can retard oxidation of other molecules, may play a role in the aging process. As described by Ames, B. N., Shigenaga, M. K. & Hagen, T. M. (1993) Oxidants, Antioxidants, and the Degenerative Diseases of Aging, *Proc. Natl. Acad. Sci. USA.* 90: 7915-7922, oxidative stress is implicated in the aging process. Oxidative stress appears to result from too low levels of antioxidants, which inhibit antioxidant enzymes. Oxidative stress is believed to damage or kill cells, and may be a partial causation in the development of many chronic and degenerative diseases including cancer, heart disease, and neuronal degeneration such as Alzheimer's and Parkinson's diseases. It is known that reactive oxygen species can damage biological molecules such as proteins, lipids, and DNA. Although the human body has developed a number of systems to eliminate free radicals from the body, the elimination process is not 100% efficient.

It is known in the art to test ORAC values, which values are considered to be a reliable parameter for measuring the antioxidant capacity of a food, drink or supplement. An oxygen radical absorbance capacity (ORAC) test method was initially developed by the U.S. Dept. of Agriculture Research Service in Boston, Mass. to quantify antioxidants that can prevent formation of reactive oxygen species (ROS). More specifically, ORAC values are determined by comparatively measuring antioxidant activity and peroxyl radicals. These measurements indicate how many free peroxyl radicals can be absorbed by a given antioxidant. These data are compared to a standard, e.g., a water-soluble vitamin E analog (Trolox) standard.

Brunswick Laboratories of Norton, Mass. 02766 is an industry leader in providing standardized measurements of antioxidant capacity against the peroxyl radical, so-called hydrophilic ORAC value testing. This industry-recognized and commonly used method was used in obtaining all μmol TE/g hydrophilic-ORAC values referred to herein. However commencing in approximately mid-2009 Brunswick Laboratories began to develop another method for total ORAC testing in which five primary free radicals are examined: peroxyl (as before), but also hydroxy, peroxynitrite, singlet oxygen, and superoxide anion. This new measurement technique has not been widely adopted and the older hydrophilic peroxyl radial remains the industry standard. Generally a test specimen will report a substantially higher ORAC value with the newer experimental measurement (so called total ORAC value) than with the industry standard hydrophilic against peroxyl radical method. Assume that a specimen has a value of say 15,000 μmol TE/g as determined using the traditional industry standard method of measuring hydrophilic-ORAC values. Testing the same specimen with the newer so-called total ORAC value technique would generally result in a higher ORAC value, often a very substantially higher value. This is because the experimental measurement technique includes, in addition to a contribution from peroxyl radicals, contributions from each of the other four radicals, which can yield a higher total ORAC value. All values of μmol TE/g referred to herein are obtained using the traditional industry standard method of measuring hydrophilic-ORAC values, and it is understood that values for the same specimen would generally be even higher if measured by the newer so-called total ORAC value method. ORAC value measurements made with either method are usually reported as micro mole Trolox Equivalents (TE) per gram or as μmol TE/g.

It is also known in the art to test ORAC values by extracting antioxidants present in a sample, and then adding a fluorescent probe and a free radical generator to the extract. The time variance of fluorescence intensity decay of the fluorescent probe in the presence of the sample is determined. One can then calculate the antioxidant capacity of the sample based upon fluorescence intensity decay of the probe in the presence of the sample.

Based on the most current dietary recommendations by the U.S. Dept. of Agriculture, research suggests that 3,000 to 5,000 ORAC units/day should be provided by food and/or supplements to have a significant impact on plasma and tissue antioxidant capacity. However, the daily diet consumed by the majority of the U.S. population does not provide adequate antioxidant protection. Some exemplary ORAC scores for common vegetables and fruits are as follow, where the units are μmol TE/g: raw watermelon 1.42, raw carrots 6.66, raw orange juice 7.2, raw bananas 8.79, raw apricots 11.15, raw white or green grapes 11.18, brewed green tea 12.53, raw red grapes 12.60, commercial reduced fat milk 12.63, raw alfalfa sprouts 15.10, red grape juice 17.88, pumpernickel bread 19.63, raw Fiji apples with skin 25.89, raw figs 33.83, red table wine 38.73, raw plums 62.59, fresh peppermint 139.78, raw ginger root 148.40, cranberry extract 151, pecan nuts 179.40, crude rice bran 242.87, yellow mustard seed 292.57, green tea powder 814, black tea powder 927, sorghum 1008.00, vitamin E 1,200, chockberry extract 2,087, ground cloves 3,144.46, raw sumac bran 3124.00, bilberry extract 4,800, and vitamin C 5,000.

It will be appreciated from the above that consuming the recommended 3,000 to 5,000 ORAC units daily can be challenging. While consuming 4.2 g of vitamin E, or 1 g of vitamin C can supply 5,000 ORAC units, in general most diets fall substantially short of the recommended 3,000 to 5,000 ORAC units per day. Simply stated, there is no single supplement or food that can provide. ORAC values in the 10,000 μmol TE/g range, let alone ORAC values in the range of at least about 10,000 μmol TE/g to about 30,000 μmol TE/g.

Thus there is a need for a process by which food stuffs and nutritional dietary antioxidant supplements can be produced with exceedingly high ORAC values in the range of at least about 10,000 μmol TE/g to about 30,000 μmol TE/g. Preferably the raw input material for such process should be commonly available and trusted by the public at large, grapes, for example. Further, the produced high ORAC value food stuffs and nutritional supplements should be substantially neutral in taste, readily soluble, and available in liquid and/or powdered form. Finally, the process should allow for tailoring the ORAC value of the food stuff and nutritional supplement being produced.

The present invention provides such a process, as well as exceedingly high ORAC value food stuffs and nutritional dietary antioxidant supplements produced by such process.

SUMMARY OF THE INVENTION

An overview of relevant terminology may be useful at this juncture. Raw grape starting material contains desired active ingredients as well as undesired inactive ingredients. The desired active ingredients are polyphenols and monomeric phenols, characterized by typically weak polar compounds that have relatively large molecules. By contrast, the undesired inactive ingredients are characterized by smaller molecules or polar compounds that bind weakly and have relatively smaller molecules. The undesired presence of inactive ingredients degrades or lessens the sought after high concentration of active ingredients. Thus the various steps carried out by the present invention are intended to produce a preferably high concentration of the desired active ingredients, while separating out the inactive ingredients. As used herein, the term "active crude grape extract" refers to an intermediate product created during the overall method of generating the desired high ORAC material. This extract includes desired polyphenols and monomeric phenols ("active ingredients") but is "crude" in the sense that it also contains other undesired material ("inactive ingredients"), mixed or dissolved, that is still present in the extract. Exemplary undesired materials in the active crude grape extract may include non-phenolic compounds that are naturally present in grape material, grape residues. The undesired materials may also include some proteins, fiber, and perhaps dirt and other impurities that survived general cleaning of the raw grape material when harvested. In one embodiment, whole grapes are processed to produce an extract highly concentrated in polyphenols, the extract having an ORAC value and antioxidant characteristics that advantageously may be controlled during processing. The extract, which may be powder or liquid, can exhibit ORAC values in the range of about 10,000 μmol TE/g to about 30,000 μmol TE/g and may be added to food supplements, foodstuffs and the like to substantially enhance beneficial antioxidant capacities.

Preferably grape fruit, skin, and/or seeds are initially dried, and soaked in an organic solvent, preferably ethanol, at elevated temperature. So doing initiates and facilitates dissolving and extracting of the dried grape raw material to yield a crude grape extract solution containing high content of polyphenol and monomeric phenols. The solvent is removed and the crude grape extract solution is at least partially separated from inactive residues, for example, using a centrifuge. Now substantially free from solid residues, the crude grape extract solution is run through a macroporous absorbent resin so that desired active ingredients are absorbed, while other material is passed substantially unabsorbed. The resin-absorbed material is then washed with increasing concentrations of organic solvent, preferably ethanol. Initially at least one low concentration washing, preferably about 5% to 15% (by volume, denoted v/v) removes impurities and perhaps some low concentration active ingredients. Next a washing with high concentration organic solvent, preferably ethanol, preferably about 80% (v/v), dissolves and carries away the desired active ingredients to provide an intermediate grape extract. As described later herein, refining and concentration of this intermediate grape extract is sufficient to yield an acceptably high desired ORAC value.

The solvent, e.g., ethanol, is then removed. Next the intermediate grape extract solution is refined, preferably in a refining tower that includes an ion exchange resin and a silicon isolation resin. During refinement, different active compounds are absorbed into different regions of the silicon isolation resin, and become isolated due to their different running speeds. In practice, the desired active ingredients are most concentrated in the middle region of the silicon resin and are collected during washings with an organic solvent, preferably ethanol, preferably about 30% (v/v). The collected desired extract solution includes concentrated polyphenols and monomeric phenols typically sufficient to meet the desired ORAC value requirement. If the desired ORAC value is not met, further refinement preferably is carried out to yield higher ORAC value material. The desired high ORAC extract solution is then spray dried, tested, and packaged. The extract powder exhibits exceptionally high ORAC value, relatively good solubility, and has a very mild favor profile and lends itself to a very wide range of beneficial antioxidant applications.

Other features and advantages of the invention will appear from the following description in which the preferred embodiments have been set forth in detail, in conjunction with the accompany drawings.

BRIEF DESCRIPTION OF THE DRAWING

FIG. 1 depicts an exemplary method for producing high ORAC value extract, according to embodiments of the present invention.

DETAILED DESCRIPTION OF THE PREFERRED EMBODIMENTS

In overview, embodiments of the present invention process preferably grape material (grape skin, and/or grape seed, and/or grape fruit) to produce an extract that is highly concentrated in polyphenols. Grapes have been found to be excellent raw material in providing the desired high polyphenol concentrate. Further processing yields an extract that may be in powder or solution form, is soluble, and is substantially mild in taste. This extract can be formulated into dietary supplements, including capsules, tablets, powders, solutions, gels, suspensions, creams, gels, and the like. ORAC value and antioxidant capacity of nutraceuticals, foods and/or beverages may be substantially enhanced by addition of the extract. Processing allows tailoring of the ORAC value of the extract with a range of at least about 10,000 μmol TE/g to about 30,000 μmol TE/g. It will be appreciated that such ORAC values are substantially higher than presently known food stuffs and nutritional supplements.

Referring now to FIG. 1, a preferred embodiment of the present invention begins with grape material, e.g., grape skin, and/or grape seed, and/or grape fruit. Applicants have found that grape material yields the desired high concentration of polyphenols that is desired for the present invention. At step 10 in FIG. 1, the raw grape materials obtained from the supplier are dried, preferably sun dried, until at the end of step 10 the material contains typically <10% water by weight.

At method step 20, an extraction process is carried out, preferably by soaking to dissolve the dried raw materials received from step 10 in an organic solvent, preferably ethanol, and applying heat to facilitate the extraction of active ingredients from the raw grape material from step 10. Applicants chose ethanol is a preferred organic solvent in that it is good agent for extracting grape polyphenols and monomeric phenols, it is relatively easy to remove, and in general its properties are reasonably well understood. At various locations within this application, although ethanol is used as a preferred solvent, it is to be understood that some other organic solvent might instead be used. Application of heat enables the desired active ingredients in the raw grape materials to be more completely dissolved in the ethanol. More particularly, the somewhat dry grape material from step 10 is mixed with ethanol in a concentration of about 25% to about 90% (v/v), and preferably about 70% (v/v), and then heated. Heating is carried out with a temperature preferably at about 70° C., but may be carried out at about 30° C. to about 90° C. Heat is applied for about 1 hour to about 7 hours. In one embodiment, method step 20 includes soaking the grape material from step 10 with about 70% ethanol (v/v) at a weight ratio of grape mixture: ethanol of about 1:7. This soaking preferably is carried out in a multiple functioning extraction tank, preferably for about 2 hours at a temperature of about 70° C. This initial soaking is then followed by use of ethanol at a grape mixture: ethanol ratio of about 1:5 for another 2 hours, still at a temperature of about 70° C. Upon conclusion of this extraction regime, the crude grape extract obtained from method step 20 will be a solution substantially high in phenolics extract. By substantially high, it is meant that there will be about 70% to about 85% polyphenols, with greater than about 8% to about 15% monomeric phenols, the percentages being by weight (e.g., wt/wt).

At method step 30, remaining ethanol is removed from the extract solution and recovered, preferably by evaporation using an external circulation evaporator machine, for example, a WZS-series concentrator with triple-effect energy conservation circulation, made by Jiangsu Changshu City Pharmacy & Chemical Plant Equipment of Jiashu, China. Preferably the external circulation vacuum pressure is controlled within a range of about 0.04 Mpa to about 0.095 Mpa (pressure may vary within this range or may be held steady at one pressure within this range), with evaporation temperature controlled within a range of about 55° C. to about 70° C., for a duration of about 3 hours. Upon conclusion of method step 30, ethanol residue in the solution preferably will be less than about 2.0% (wt/wt), and the extract solution will have a relative density of about 1.15 when measured at 65° C. after removal of the ethanol.

Commonly, heavy metals may be present in the extract solution, and will have come mainly from the environment from which the raw grape materials were obtained, e.g., the soil, the irrigation water, etc. Thus, at method step 40, the extract solution from step 30 preferably is run through an ion exchange resin unit that absorbs heavy metals present in the solution. An exemplary ion exchange resin unit is model 1700, manufactured by Xi'an Sun Resin Technology Ltd, located in Xi'an, China. Preferably relatively little or no active ingredients are lost during step 40, through the use of clean water (e.g., suitable for drinking) to wash the resin, with the same quantity of water preferably being used as the resin volume. By way of example, if a flow rate of about 5.5 L/Min is used, and the resin volume is 1,500 L, step 40 will take about 4.5 hours. At the conclusion of step 40, after passing through the ion exchange resin unit the collected extract solution will have a relatively low level of heavy metals. Any remaining heavy metal should meet the final quality control specification for the final high-ORAC product, for example, total heavy metals ≦8 ppm. To ensure quality control, preferably repeat testing for heavy metals occurs later on at method step 90.

At this point in the process, polyphenols and monomeric phenols from the original raw grape material are the desired active ingredients in the obtained extract solution. Also present in the crude extract solution, mixed or dissolved, will be inactive ingredients and grape residues, including some proteins, fiber, perhaps dirt and other impurities present when the raw grape material was harvested that escaped general cleaning. At method step 50, the undesired grape residue in solid form is separated from the crude grape extract solution, preferably using centrifugal separation although other separation techniques might be used instead. The separation centrifuge preferably is operated at controlled revolution speeds. Typically, an, initial rotational speed of about 1,000 rpm is carried out for perhaps 5 minutes, followed by further centrifugal separation at a higher speed, for example about 14,000 rpm for an additional 10 minutes. If rotational speed is too fast, e.g., >20,000 rpm, some active ingredients may be lost. Typically separation at method step 50 results in a desired solution layer of supernatant liquid. Within this supernatant liquid is the grape extract solution containing substantially all of the desired active ingredients, as well as some undesired or inactive material. Also present is a solid pellet layer on the bottom that contains the undesired solid residues, and preferably is discarded at this juncture.

Following method step 50, the grape extract is substantially free from solid residues including grape raw materials and is in a solution with a characteristic pH of about pH 4.5 to about pH 5.0. In step 60, the output solution from step 50 is run through a macroporous absorbent resin at a flow rate of about 5.5 L/min. The macroporous absorbent resin has pores sized approximately 150 nm to about 700 nm and selectively absorbs organic compounds from the aqueous solution. An exemplary of such macroporous absorbent resin unit is model 700, manufactured by Xi'an Sun Resin Technology Ltd, located in Xi'an, China. In an exemplary bulk production unit, the absorption resin volume will be about 1,500 L. As described below, the resin absorbs the active crude grape extract, which is then collected using ethanol, as described with respect to step 70.

During method step 60, the resin will absorb the desired active ingredients, namely the polyphenols and monomeric phenols, from the grape extract solution obtained from method step 50. As a practical matter, the resin may also absorb some inactive ingredients, e.g. sugar, some proteins and some soluble fibers, if present. More specifically, the desired active ingredients are typically weak polar compounds that have relatively large molecules, and therefore can be easily absorbed by the macroporous absorption resin. By contrast, the inactive ingredients are characterized by smaller molecules or polar compounds that weakly bind or do not bind to the resin, and are discarded during step 60. In practice, it is not until completion of step 70 that the more purified grape extract solution with active ingredients is actually available.

At method step 70, the absorbent resin with absorbed active ingredients within is washed several times with different concentrations of ethanol solvent to yield the intermediate grape extract solution with its more purified active ingredients. Initially a preferably two-step washing is carried out using low concentration 5% and 15% (v/v) ethanol to wash out inactive compounds that bind weakly or not at all to the macroporous absorption resin. Thus, what is washed out and discarded during these initial two washings will primarily be inactive ingredients, e.g. some proteins, sugars, and typically some low concentration active ingredients. Preferably the volume of ethanol used for both the 5% and the 15% washing is about the volume of the macroporous resin, here about 1,500 L, with an exemplary flow rate of about 1.5 L/min to about 6 L/min, and preferably about 5.5 L/min.

In method step 70, after the initial two washings with relatively low concentration (e.g., 5%, 15% v/v) ethanol have carried away poorly bound compounds, impurities and perhaps low concentration active ingredients, it remains to actually obtain the desired concentrated active ingredients. This is accomplished with a third washing of the macroporous absorbent resin with a relatively high concentration of ethanol, about 75% to about 85% and more preferably about 80% (v/v), again at a flow rate of about 5.5 L/min. In practice, the total volume of 80% (v/v) ethanol used in this final step 70 washing typically will exceed the volume of the macroporous resin, and is preferably about 150% greater, e.g., about 2,300 L. This final washing yields an intermediate grape extract with high concentration active ingredients, which extract should exhibit an ORAC value of at least about 50% to about 80% of the specification ORAC value, typically 10,000 μmol TE/g or higher. Thus, the ethanol washings at method step 70 remove impurities and/or low concentration compounds, and enable collection of the desired active ingredients in concentration sufficiently high to produce the desired high ORAC values.

At method step 80, the ethanol, e.g., the high concentration typically 80% v/v ethanol, is removed and may be recovered, preferably by evaporation as described at step 30. Exemplary evaporation is under a vacuum pressure of about −0.04 MPa to about −0.095 MPa (pressure may vary within this range or may be at a constant pressure within this range) with a distilling temperature controlled to be within about 50° C. to about 80° C. The residue of Ethanol concentration obtained here should be lower than around 1.0% (wt/wt).

At method step 90, the intermediate grape extract solution with concentrated active ingredients is refined at least once. A preferred exemplary mechanism for step 90 is a refining tower, preferably a refining tower with two resins within: preferably an ion exchange resin on the top and a silicon isolation resin on the bottom. The same type of ion exchange resin as described with respect to method step 40 can be used at step 90. An exemplary silicon isolation resin is silicon isolation resin model 1400, manufactured by Xi'an Sun Resin Technology Ltd., of Xi'an, China. It will be recalled that heavy metals were removed at method step 40. Preferably during method step 90, after the concentrated grape extract solution is run through the ion exchange resin, remaining heavy metals are removed to ensure meeting product specification for heavy metal levels.

During method step 90, as the grape extract solution continues to run through the refining tower, different active compounds are absorbed into different regions of the silicon isolation resin, and become isolated due to different running speeds of different compounds within the grape extract solution. The desired active ingredients are most concentrated in the middle region of the silicon resin. The refining tower preferably is a long and narrow column, e.g., about 20 M in height by about 3 M in diameter, to allow good isolation and longer ethanol washing time. The refining tower can control and enable longer washing times at a target region, typically mid-height within the tower, using steerable spray heads that can be aimed upwards or downwards when spraying ethanol. The concentrated high ORAC value compounds (polyphenols and monomeric phenols) will be found within these mid-height regions. Preferably two washing steps are used to collect these various active ingredients. During an initial washing step, a relatively low concentration of ethanol of about 25% to about 35% (v/v) and preferably 30% (v/v) is used, and an extract solution with concentrated polyphenols and monomeric phenols is collected. Exemplary volume used is about 10,000 L, which is about the volume of the silicon isolation resin within the refining tower. It is this collection from the initial washing step that yields the desired high ORAC (e.g., >10,000 ORAC μmol TE/g) extract solution that is further processed in method steps 100-130, as shown in FIG. 1. This desired high ORAC extract solution will typically comprise about 75% to about 95% (wt/wt) polyphenols, and about 15% to about 35% (wt/wt) monomeric phenols. During a second washing step, preferably about 70% to about 85% (v/v) and more preferably 80% v/v ethanol is used to collect extract solution that is concentrated with proanthocyanidins, which solution can be commercially useful in unrelated applications. The concentrations and make up of these two washings may be altered somewhat, if desired.

Preferably ORAC value testing and testing for polyphenols and monomeric phenols is carried out as part of method step 90. If the concentrated polyphenols and monomeric phenols extract from method step 90 exhibit an acceptably high ORAC value, e.g., ≧10,000 μmol TE/g, the concentrate is ready for spray drying at method 100, after the ethanol is removed as part of the refinement step 90. Consider, however, the case where the concentrated polyphenols and monomeric phenols extract from method step 90 do not initially exhibit the desired ORAC value following refinement, e.g., perhaps a target ORAC value of 15,000 μmol TE/g is desired whereas an actual ORAC value of 10,000 μmol TE/g is produced. In this situation, a slower flowrate at method step 90 may be used, e.g., perhaps 2.0 L/min rather than 2.5 L/min. A faster flowrate perhaps about 5 L/min may be used if the measured ORAC value at method step 90 is close to the target production ORAC value. If required, refinement at step 90 can be carried out repeatedly until the concentrate extract produced at method step 90 meets specification. In any event, once the tested ORAC value of the concentrate extract from method 90 is acceptably high, e.g., 15,000 μmol TE/g if that is the specification target value, the material, solution or paste, is ready for spray drying at step 100 after the ethanol is removed. It is understood that at this point in the process, the ethanol that has been used to wash and collect the desired active ingredients has served its purpose and will now be removed. Removing or recovery of ethanol is carried out, preferably using method steps 30 and 80, as described. In practice, some ethanol will typically remain despite removal according to method steps 30 and 80. Any remaining or residual ethanol should be relatively low in concentration, e.g., <0.1% (wt/wt).

Spray drying at method step 100 preferably is carried out using a spray drying tower. In bulk production, the spray drying tower is about 7 to 8 meters in height with a diameter of about 3 meters. The density of the extract solution to be run through the spray drying tower will be about 15 as measured with a Baume density meter. The flow rate running speed is controlled to be about 5 L/min. Preferably temperature of the entrance air flow at step 110 is controlled to at least about 180° C., and the exit temperature is about 80° C. Following step 110, the spray-dried powder material should have moisture content of <5% (wt/wt), or as otherwise specified. It is understood that other spray drying tower configurations might be used, as well as other flowrates, and entrance and exit temperatures.

At method step 110, spot testing of the production run is undertaken in real-time to confirm that what is now being produced meets the general specification. During the production run, the desired dried grape concentrate is tested at step 110 for several factors including ORAC value, polyphenols, and monomeric phenols. Real-time testing for ORAC and phenolics preferably is performed on powder form samples. During real-time production, a solution or paste form of the intermediate product is preferably dried at about 200° C. for about 10 minutes to yield a powder material for the testing at step 90. In fact, preferably a powder form of the material is used for testing at subsequent step 130.

At method step 120, the high ORAC value grape concentrate preferably is crushed and mixed to yield a uniform blend of powder, and packaged. Final quality control testing is carried out at method step 130 to ensure desired potency, including desired ORAC value, percentage of polyphenols and monomeric phenols, heavy metal and microbial levels, as well as some physical characteristics, e.g. bulk density and water solubility. The final output following step 130 will be a very high ORAC value grape extract that may be provided in powder form, or by adding distilled water to the powder, in liquid form. By very high ORAC value it is meant that the grape extract produced by the present invention will have an ORAC value of 10,000 μmol TE/g or greater, and preferably in a range of at least about 10,000 μmol TE/g to about 30,000 μmol TE/g. Of course, if desired the present invention could be used to produce products with lower ORAC values, e.g., <10,000 μmol TE/g.

The ORAC value of final products produced according to the present invention as shown in FIG. 1 was verified at Brunswick Lab, located in Norton, Mass. Brunswick Lab verifies ORAC values by adding a fluorescent probe to the extract being tested, and then monitoring fluorescence intensity decay to determine ORAC values. This method used by Brunswick Lab is described in U.S. Pat. No. 7,132,296. Table 1 below shows Brunswick Lab measured data for various production lots of high ORAC value grape material, according to the present invention.

TABLE 1

| Production lot number | Measured ORAC Value (μmol TE/g) |
|---|---|
| 20071002 | 14,061 |
| 20070519 | 16,416 |
| 20070917 | 16,624 |
| 20070919 | 14,878 |
| 20071118 | 15,519 |

The very high ORAC concentrate produced by the present invention has a mild tea-like taste, and is very soluble in water, e.g., >0.5 g/100 mL water, and may be added to foodstuffs, to nutritional or dietary supplements. Table 2 shows solubility of the final product in different solvents, where percentages are by volume of the constituents stated.

TABLE 2

| SOLVENT | SOLUBILITY |
|---|---|
| Deionized water | Soluble |
| 100% ethanol | Soluble |
| 25%:75% alcohol:water | Soluble |

TABLE 2-continued

| SOLVENT | SOLUBILITY |
|---|---|
| 50%:50% alcohol:water | Soluble |
| 75%:25% alcohol:water | Soluble |
| Butylene glycol | Soluble |
| Propylene glycol | Soluble |
| Olive oil | Suspension |
| SLES surfactant | Suspension |
| Silicon oil | Insoluble |
| Isononyl isononanoate | Insoluble |

The concentrate may be packaged in a variety of forms, including without limitation, capsules, tablets, powders, solutions, gels, suspensions, creams, and the like. Without limitation, the extract, whether it is in powder or liquid form, may be added to nutraceuticals, foods, and/or beverages to increase the ORAC value and antioxidant capacity. Adding concentrate produced by the present invention to food, nutritional supplements, drink, etc. will readily enable consumers to achieve the recommended intake of 5,000 ORAC units per day, at low cost, and without having to consume large quantities of food or drink.

Modifications and variations may be made to the disclosed embodiments without departing from the subject and spirit of the present invention as defined by the following claims.

What is claimed is:

1. A method to produce an antioxidant grape extract exhibiting an ORAC value of at least 10,000 μmol TE/g, the method including the following steps:
 (a) drying grape material including at least one of (i) grape fruit, (ii) grape skin, and (iii) grape seed;
 (b) creating an active crude grape extract solution that includes polyphenols and monomeric phenols, as well as inactive ingredients, by dissolving dried said grape material in ethanol;
 (c) employing means for separating from said solution created at step (b) at least a fraction of said active crude grape extract without substantially retaining said inactive ingredients; and
 (d) refining, at least once, active crude grape extract separated at step (c) to collect an extract solution containing polyphenols with a concentration about 70% to about 95% by weight and containing monomeric phenols with a concentration of about 10% to about 45% by weight, to produce said antioxidant grape extract exhibiting an ORAC value of at least 10,000 μmol TE/g.

2. The method of claim 1, wherein step (b) includes at least one of (i) dissolving dried said grape material in ethanol having a concentration in a range of about 25% to about 90% by volume, (ii) dissolving dried said grape material with about 70% ethanol by volume at a volume ratio of grape mixture:ethanol of about 1:5 to 1:8, (iii) dissolving dried said grape material with about 70% ethanol by volume at a volume ratio of grape mixture:ethanol of about 1:7 with a grape mixture:ethanol ratio of about 1:5 for 4 hours, (iv) dissolving dried said grape material with about 70% ethanol by volume at a volume ratio of grape mixture:ethanol of about 1:5 to 1:7 for two hours followed by a grape mixture:ethanol ratio of about 1:5 for two hours at a temperature of about 70° C., (v) heating said ethanol to a temperature in a range of about 30° C. to about 90° C., (vi) dissolving in said ethanol for a duration of about 1 hour to about 7 hours, (vii) creating said active crude grape extract with at least about 70% polyphenols by weight, (viii) creating said active crude grape extract solution with at least about 8% to about 15% monomeric phenols by weight, and (ix) creating said active crude grape extract using a multiple functioning extraction tank for about 2 hours at a temperature of about 70° C.

3. The method of claim 1, further including centrifugally separating active crude grape extract created at step (b) to a yield a solution containing substantially all said polyphenols and monomeric phenols.

4. The method of claim 1, wherein at step (c) said means for separating has at least one characteristic selected from a group consisting of (i) said means for separating functions at least in part based upon binding characteristics of said polyphenols and monomeric phenols that are stronger than binding characteristics of said inactive ingredients, (ii) said means for separating includes a macroporous absorption resin to which at least a fraction of said active ingredients bind, while a substantial fraction of said inactive ingredients fail to bind, (iii) said means for separating uses a macroporous absorption resin having at least one characteristic selected from a group consisting of (I) a resin defining openings in a range of about 150 nm to about 700 nm, (II) a resin absorption volume of about 1,500 L, and (III) a resin flow rate of about 5.5 L/min, and (iv) said means for separating includes a macroporous absorption resin to which at least a fraction of said active ingredients bind, while a substantial fraction of said inactive ingredients fail to bind, and said means for separating further includes at least a first washing of said macroporous absorption resin in ethanol having concentration less than 30% by volume, and a second washing in ethanol having a concentration at least 50% by volume, to obtain from said macroporous absorption resin active crude grape extract separated during step (c).

5. The method of claim 1, where step (d) includes using a separation resin to at least partially isolate different active ingredients in said active crude grape extract, and washing said separation resin in ethanol having a concentration ranging from about 15% to about 45% by volume.

6. The method of claim 4, wherein said means for separating includes a macroporous absorption resin, and further including intermediate step (c) and step (d) at least a first washing and a second washing of said macroporous absorption resin wherein at least one of said first washing and said second washing has at least one characteristic selected from a group consisting of (i) said first washing is with a concentration of ethanol in a range of about 5% to about 15% by volume, (ii) said first washing is with a concentration of ethanol in a range of about 5% by volume and followed by a washing with 15% ethanol by volume, (iii) said first washing is with a concentration of ethanol sufficiently low to dissolve inactive ingredients and impurities without dissolving substantial active ingredients absorbed by said macroporous absorption resin, (iv) said first washing uses a volume of ethanol approximating volume of said macroporous absorption resin, (v) at least one of said first washing and said second washing is at a flow rate of about 1.5 L/min. to about 6 L/min., (vi) at least one of said first washing and said second washing is at a flow rate of about 5.5 L/min., (vii) said second washing is with a concentration of ethanol of about 75% to about 85% by volume, (viii) said second washing is with a concentration of ethanol of about 80% by volume, (ix) said second washing uses a volume of ethanol approximately 150% volume of said macroporous absorption resin, and (x) obtained said crude grape extract includes at least one of polyphenols in a range of about 70% to about 90% by weight, and monomeric phenols in a range of about 10% to about 20% by weight.

7. The method of claim 1, wherein step (d) includes at least one of (i) use of a refining tower, (ii) use of a refining tower including two resins, (iii) use of a refining tower including at least one of an ion exchange resin and a silicon isolation resin, (iv) use of a refining tower including an ion exchange resin disposed above a silicon isolation resin, and (v) using a refining tower including a silicon isolation resin and operated to cause different active compounds to be absorbed into different regions of said silicon isolation resin.

8. The method of claim 7, wherein step (d) is carried out with a refining tower and further includes washing with ethanol to collect active ingredients from said refining tower, said washing having at least one characteristic selected from a group consisting of (i) said washing uses ethanol having a concentration of about 25% to about 35% by volume, (ii) said washing uses ethanol having a concentration of about 35% by volume, (iii) said washing includes a first washing using ethanol having a concentration of about 25% to about 35% by volume followed by a second washing using ethanol having a concentration of about 70% to about 85% by volume ethanol, (iv) said washing includes a first washing with ethanol having a concentration of about 25% to about 35% by volume followed by a second washing with ethanol having a concentration of about 80% by volume, and (v) said refining tower includes a silicon isolation resin and said washing uses ethanol having a volume approximating volume of said silicon isolation resin.

9. The method of claim 1, further including at least one of (i) repeating step (d) as required to obtain said antioxidant grape extract having a target ORAC value of at least 10,000 µmol TE/g, and (ii) drying and quality control testing antioxidant grape extract resulting from step (d).

10. An antioxidant grape extract exhibiting an ORAC value of at least 10,000 µmol TE/g produced according to the following method:
  (a) drying grape material including at least one of (i) grape fruit, (ii) grape skin, and (iii) grape seed;
  (b) creating an active crude grape extract solution that includes polyphenols and monomeric phenols, as well as inactive ingredients, by dissolving dried said grape material in ethanol;
  (c) employing means for separating from said solution created at step (b) at least a fraction of said active crude grape extract without substantially retaining said inactive ingredients; and
  (d) refining, at least once, active crude grape extract separated at step (c) to collect an extract solution containing polyphenols with a concentration about 70% to about 95% by weight and containing monomeric phenols with a concentration of about 10% to, about 45% by weight, to produce said antioxidant grape extract exhibiting an ORAC value of at least 10,000 µmol TE/g.

11. The antioxidant grape extract of claim 10, wherein step (b) includes at least one of (i) dissolving dried said grape material in ethanol having a concentration in a range of about 25% to about 90% by volume, (ii) dissolving dried said grape material with about 70% ethanol by volume at a volume ratio of grape mixture:ethanol of about 1:5 to 1:8, (iii) dissolving dried said grape material with about 70% ethanol by volume at a volume ratio of grape mixture:ethanol of about 1:7 with a grape mixture:ethanol ratio of about 1:5 for 4 hours, (iv) dissolving dried said grape material with about 70% ethanol by volume at a volume ratio of grape mixture:ethanol of about 1:5 to 1:7 for two hours followed by a grape mixture:ethanol ratio of about 1:5 for two hours at a temperature of about 70° C., (v) heating said ethanol to a temperature in a range of about 30° C. to about 90° C., (vi) dissolving in said ethanol for a duration of about 1 hour to about 7 hours, (vii) creating said active crude grape extract with at least about 70% polyphenols by weight, (viii) creating said active crude grape extract solution with at least about 8% to about 15% monomeric phenols by weight, and (ix) creating said active crude grape extract using a multiple functioning extraction tank for about 2 hours at a temperature of about 70° C.

12. The antioxidant grape extract of claim 10, further including centrifugally separating active crude grape extract created at step (b) to a yield a solution containing substantially all said polyphenols and monomeric phenols.

13. The antioxidant grape extract of claim 10, wherein at step (c) said means for separating has at least one characteristic selected from a group consisting of (i) said means for separating functions at least in part based upon binding characteristics of said polyphenols and monomeric phenols that are stronger than binding characteristics of said inactive ingredients, (ii) said means for separating includes a macroporous absorption resin to which at least a fraction of said active ingredients bind, while a substantial fraction of said inactive ingredients fail to bind, (iii) said means for separating includes using a macroporous absorption resin having at least one characteristic selected from a group consisting of (I) a resin defining openings in a range of about 150 nm to about 700 nm, (II) a resin absorption volume of about 1,500 L, and (III) a resin flow rate of about 5.5 L/min, and (iv) said means for separating includes a macroporous absorption resin to which at least a fraction of said active ingredients bind, while a substantial fraction of said inactive ingredients fail to bind, and said means for separating further includes at least a first washing of said macroporous absorption resin in ethanol having concentration less than 30% by volume, and a second washing in ethanol having a concentration at least 50% by volume, to obtain from said macroporous absorption resin active crude grape extract separated during step (c).

14. The antioxidant grape extract of claim 10, The method of claim 1, where step (d) includes using a separation resin to at least partially isolate different active ingredients in said active crude grape extract, and washing said separation resin in ethanol having a concentration ranging from about 15% to about 45% by volume.

15. The antioxidant grape extract of claim of claim 13, wherein said means for separating includes a macroporous absorption resin, and further including intermediate step (c) and step (d) at least a first washing and a second washing of said macroporous absorption resin wherein at least one of said first washing and said second washing has at least one characteristic selected from a group consisting of (i) said first washing is with a concentration of ethanol in a range of about 5% to about 15% by volume, (ii) said first washing is with a concentration of ethanol in a range of about 5% by volume and followed by a washing with 15% ethanol by volume, (iii) said first washing is with a concentration of ethanol sufficiently low to dissolve inactive ingredients and impurities without dissolving substantial active ingredients absorbed by said macroporous absorption resin, (iv) said first washing uses a volume of ethanol approximating volume of said macroporous absorption resin, (v) at least one of said first washing and said second washing is at a flow rate of about 1.5 L/min. to about 6 L/min., (vi) at least one of said first washing and said second washing is at a flow rate of about 5.5 L/min., (vii) said second washing is with a concentration of ethanol of about 75% to about 85% by volume, (viii) said second washing is with a concentration of ethanol of about 80% by volume, (ix) said second washing uses a volume of ethanol approximately 150% volume of said macroporous absorption resin, and (x) obtained said crude grape extract includes at least one of polyphenols in a range of about 70% to about 90% by weight, and monomeric phenols in a range of about 10% to about 20% by weight.

16. The antioxidant grape extract of claim 10, wherein step (d) includes at least one of (i) use of a refining tower, (ii) use of a refining tower including two resins, (iii) use of a refining tower including at least one of an ion exchange resin and a silicon isolation resin, (iv) use of a refining tower including an ion exchange resin disposed above a silicon isolation resin, and (v) using a refining tower including a silicon isolation resin and operated to cause different active compounds to be absorbed into different regions of said silicon isolation resin.

17. The antioxidant grape extract of claim 16, wherein step (d) is carried out with a refining tower and further includes washing with ethanol to collect active ingredients from said refining tower, said washing having at least one characteristic selected from a group consisting of (i) said washing uses ethanol having a concentration of about 25% to about 35% by volume, (ii) said washing uses ethanol having a concentration of about 35% by volume, (iii) said washing includes a first washing using ethanol having a concentration of about 25% to about 35% by volume followed by a second washing using ethanol having a concentration of about 70% to about 85% by volume ethanol, (iv) said washing includes a first washing with ethanol having a concentration of about 25% to about 35% by volume followed by a second washing with ethanol having a concentration of about 80% by volume, and (v) said refining tower includes a silicon isolation resin and said washing uses ethanol having a volume approximating volume of said silicon isolation resin.

18. The antioxidant grape extract of claim 10, wherein step (e) is repeated as required to obtain said antioxidant grape extract having a target ORAC value of at least 10,000 μmol TE/g.

19. An antioxidant material having a precisely controlled ORAC value of at least 5,000 μmol TE/g, produced according to the following method:
  (a) drying grape material including at least one of (i) grape fruit, (ii) grape skin, and (iii) grape seed;
  (b) creating an active crude grape extract solution that includes polyphenols and monomeric phenols, as well as inactive ingredients, by dissolving dried said grape material in ethanol;
  (c) employing means for separating from said solution created at step (b) at least a fraction of said active crude grape extract without substantially retaining said inactive ingredients; and
  (d) refining, at least once, active crude grape extract separated at step (c) to collect an extract solution containing polyphenols with a concentration about 70% to about 95% by weight and containing monomeric phenols with a concentration of about 10% to about 45% by weight, to produce said antioxidant grape extract exhibiting an ORAC value of at least 10,000 μmol TE/g; and
  (e) combining said antioxidant material with a sufficient amount of said antioxidant grape extract exhibiting an ORAC value of at least 10,000 μmol TE/g obtained at step (d), to cause said antioxidant material to have a controlled ORAC value ranging from about 5,000 μmol TE/g to at least about 10,000 μmol TE/g.

20. The antioxidant material of claim 19, wherein said antioxidant material has at least one characteristic selected from a group consisting of (i) said antioxidant material is a nutraceutical, (ii) said antioxidant material is food, (iii) said antioxidant material is a beverage, (iv) said antioxidant material is a capsule, (v) said antioxidant material is a tablet, (vi) said antioxidant material is a powder, (vii) said antioxidant material is a solution, (viii) said antioxidant material is a gel, (ix) said antioxidant material is a suspension, and (x) said antioxidant material is a cream.

21. A method to produce an antioxidant material having a precisely controlled ORAC value of at least 5,000 µmol TE/g, the method comprising the following steps:
(a) drying grape material including at least one of (i) grape fruit, (ii) grape skin, and (iii) grape seed;
(b) creating an active crude grape extract solution that includes polyphenols and monomeric phenols, as well as inactive ingredients, by dissolving dried said grape material in ethanol;
(c) employing means for separating from said solution created at step (b) at least a fraction of said active crude grape extract without substantially retaining said inactive ingredients; and
(d) refining, at least once, active crude grape extract separated at step (c) to collect an extract solution containing polyphenols with a concentration about 70% to about 95% by weight and containing monomeric phenols with a concentration of about 10% to about 45% by weight, to produce said antioxidant grape extract exhibiting an ORAC value of at least 10,000 µmol TE/g; and
(e) combining said antioxidant material with a sufficient amount of said antioxidant grape extract exhibiting an ORAC value of at least 10,000 µmol TE/g obtained at step (d), to cause said antioxidant material to have a controlled ORAC value ranging from about 5,000 µmol TE/g to at least about 10,000 µmol TE/g.

22. The method of claim 21, wherein said antioxidant material has at least one characteristic selected from a group consisting of (i) said antioxidant material is a nutraceutical, (ii) said antioxidant material is food, (iii) said antioxidant material is a beverage, (iv) said antioxidant material is a capsule, (v) said antioxidant material is a tablet, (vi) said antioxidant material is a powder, (vii) said antioxidant material is a solution, (viii) said antioxidant material is a gel, (ix) said antioxidant material is a suspension, and (x) said antioxidant material is a cream.

* * * * *